United States Patent [19]
Kroll et al.

[11] Patent Number: 6,074,540
[45] Date of Patent: *Jun. 13, 2000

[54] ELECTROCHEMICAL SOLID-STATE SENSOR FOR CHLORINE

[75] Inventors: Alla Zakhartchenko Kroll; Dieter Mähl, both of Berlin, Germany

[73] Assignee: Auergesellschaft GmbH, Berlin, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/648,655

[22] Filed: May 15, 1996

[30] Foreign Application Priority Data

May 16, 1995 [DE] Germany .............. 195 17 907

[51] Int. Cl.$^7$ ................................. G01N 27/407
[52] U.S. Cl. ................ 204/424; 204/426; 205/779.5
[58] Field of Search .................. 204/421–429; 205/783.5, 784, 784.5, 785, 778.5, 779.5; 429/30

[56] References Cited

U.S. PATENT DOCUMENTS

| | | | |
|---|---|---|---|
| 3,134,697 | 5/1964 | Niedrach .............................. | 429/30 |
| 3,764,269 | 10/1973 | Oldham et al. . | |
| 3,843,400 | 10/1974 | Radford et al. ...................... | 204/421 |
| 4,024,036 | 5/1977 | Nakamura et al. .................. | 204/295 |
| 4,492,614 | 1/1985 | Welsh .................................. | 204/421 |
| 4,526,674 | 7/1985 | Fouletier et al. .................... | 204/426 |
| 4,718,991 | 1/1988 | Yamazoe et al. ................... | 204/421 |
| 5,118,398 | 6/1992 | McElroy et al. .................... | 204/421 |
| 5,288,388 | 2/1994 | Fombon .............................. | 204/418 |
| 5,350,643 | 9/1994 | Imahashi et al. ................... | 429/30 |

FOREIGN PATENT DOCUMENTS

| | | |
|---|---|---|
| 2581762 | 5/1986 | France . |
| 35 00 088 A1 | 7/1986 | Germany . |
| 36 44 819 A1 | 9/1989 | Germany . |
| 1762214 A1 | 9/1992 | U.S.S.R. . |
| 2 117 121 | 10/1983 | United Kingdom . |

OTHER PUBLICATIONS

Gopel, W. et al. Sensors: A Comprehensive Survey. Chemical Sensor Technologies: Empirical Art and Systematic Research. Vol. 2, p. 82.

European Patent Search, Application 96107721.1. Dated Jun. 5, 1997. (Original and English translation included).

*Primary Examiner*—T. Tung
*Attorney, Agent, or Firm*—Reed Smith Shaw & McClay LLP

[57] ABSTRACT

A sensor includes a sensor electrode layer, a solid electrolyte layer and a backplate electrode layer. The contacts for the sensor electrode and the backplate electrode are integrated into the sensor electrode layer and the backplate electrode layer. The contact integrated into the sensor electrode layer is used as a diffusion barrier. A solid electrolyte is placed in the layer of the sensor electrode and the backplate electrode. The sensor functions according to the amperometric principle at ambient temperatures, and is manufactured by the cold-pressing of layers (1) to (3).

5 Claims, 1 Drawing Sheet

ELECTROCHEMICAL SOLID-STATE SENSOR FOR CHLORINE

BACKGROUND OF THE INVENTION

The invention relates to a electrochemical solid-state electrolyte sensor for measuring chlorine and a process for the manufacture of the sensor.

The use of a solid-state electrolyte sensor to detect oxygen such as in vehicle exhaust gases is known from field experience. Patent literature describes a solid-state electrolyte sensor to determine the hydrogen concentration in gas mixtures (SU-PS 11 00 555). A solid-state electrolyte sensor for an electrochemical measuring device is known from an earlier invention (SU-PS 67 05 66). These solid-state electrolyte sensors of the prior art have a low signal stability of the output signal of the sensor. The manufacture of the sensor element is complicated and a reproducibility of the properties is not guaranteed. A process and a solid-state electrolyte sensor for the detection of chlorine is known from patent DE-OS 35 00 088. The solid-state electrolyte sensor described in this patent application that works according to a potentiometric principle requires a working temperature of at least 160° C. in order to guarantee proper response times. A practical use of this solid-state electrolyte sensor is not possible with normal ambient temperatures. Another disadvantage is the complex procedure used to operate the solid electrolytic sensor that cannot guarantee the stability of the sensitivity of the sensor.

SUMMARY OF THE INVENTION

The object of the invention is the development of an electrochemical solid-state electrolyte sensor for the measurement of chlorine that has an improved signal stability and that is easier t6 manufacture compared to solid-state electrolyte sensors of the prior art.

According to the invention a solid-state electrolyte sensor for the measurement of chlorine was developed which operates on the amperometric principle and functions at ambient temperatures.

The solid-state electrolyte sensor has three layers consisting of the sensor or working electrode, the solid-state electrolyte and the reference electrode that are arranged side by side. The contacts for the sensor electrodes and the reference electrode were integrated in the respective layers of the electrodes.

According to the invention the electrochemical solid-state electrolyte sensor for the measurement of chlorine is manufactured in that the layers are filled into a form and cold-pressed. Other advantageous embodiments of the invention are described in the sub-claims.

DETAILED DESCRIPTION OF THE PRESENTLY PREFERRED EMBODIMENTS

Figure 1:
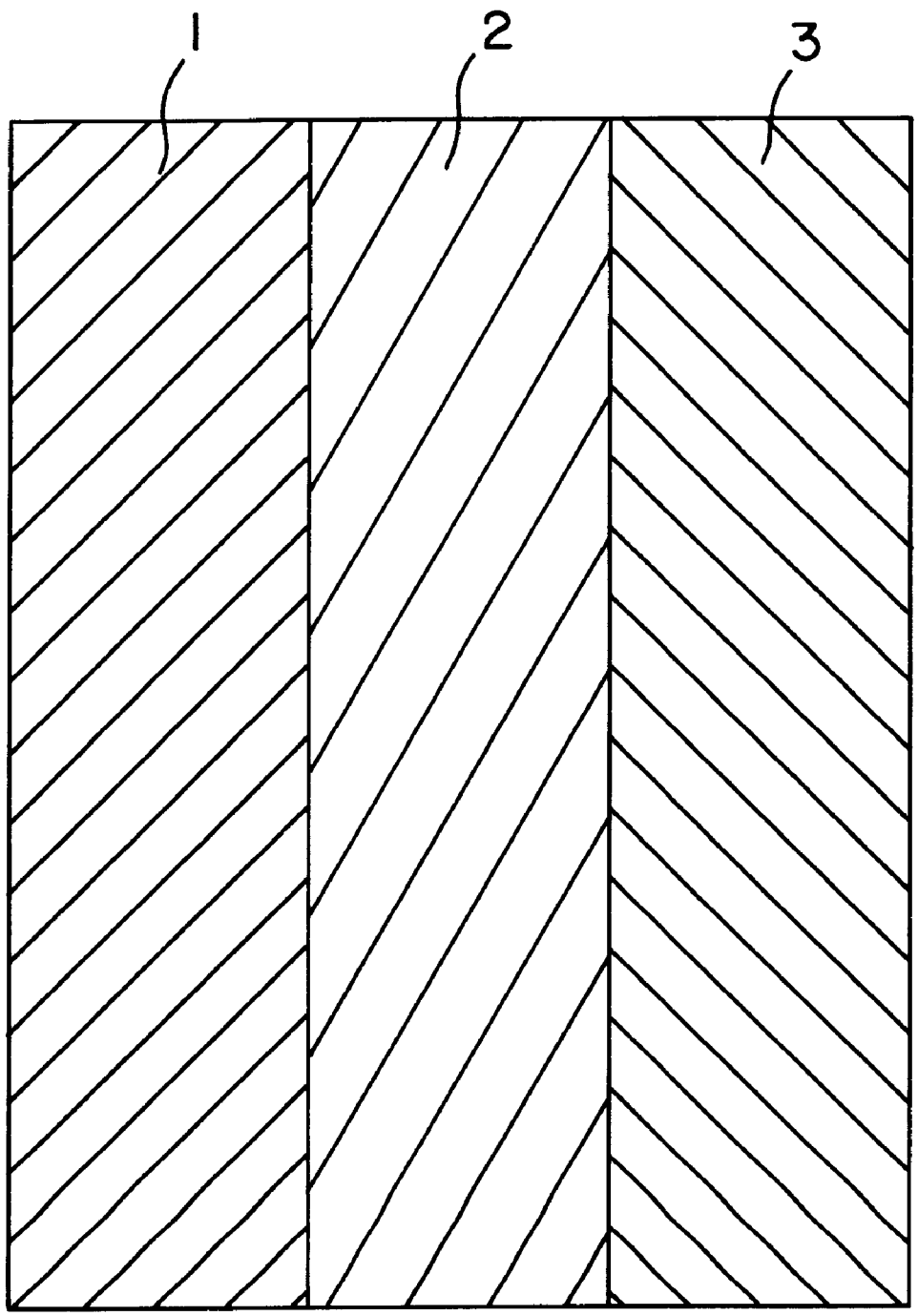
FIG. 1 is a schematic view of the electrochemical solid-state electrolyte sensor of the present invention.

An embodiment of the invention is shown in the drawing. The figure shows a schematic of the electrochemical solid-state electrolyte sensor for the measurement of chlorine. The solid-state electrolyte sensor has layers consisting of the sensor electrode (1), the solid electrolyte (2) and the reference electrode (3). The layers are placed side by side. The contact is integrated into the layer of the sensor electrode (1) and the contact for the reference electrode (3) is integrated in that layer. The contact that is integrated into the sensor electrode (1) is used simultaneously as a diffusion barrier. The layer of the reference electrode (3) with the integrated contact consists of a mixture of a macrocyclic compound of the transition metal and a conductive material. In the layer of the sensor electrode (1) and the reference electrode (3) there is a solid-state electrolyte. The layer for the solid-state electrolyte (2) consists of a material with good conductivity for protons, such as that known by the german term Wolframatophosphoräure-Hydrat, $H_3$ $[P(W_3O_{10})_4] \times H_2O$. The layer of the sensor electrode (1) with the integrated contact consists of a catalytically active and a conductive material. The layer of the sensor electrode (1) is preferably of a noble metal.

For the manufacture of the solid-state electrolyte sensor according to FIG. 1 the layers (1) to (3) are filled into a form and cold-pressed. The layers (1)–(3) are pressed briefly after being filled into the form and are then pressed into the solid-state electrolyte sensor.

We claim:

1. An electrochemical solid-state electrolyte sensor for measuring chlorine comprising:

a sensor electrode comprising a sensor contact associated therewith;

a solid-state electrolyte; and a reference electrode comprising a backplate contact associated therewith, the sensor electrode, the solid-state electrolyte and the reference electrode comprising three layers arranged in a side-by-side relationship;

wherein the electrochemical solid-state electrolyte sensor is adapted to function according to the amperometric principle at ambient temperatures;

wherein each of the sensor electrode and the reference electrode comprises an amount of solid-state electrolyte disposed therewithin;

wherein the reference electrode comprises a mixture of a macrocyclic compound of a transition metal and a conductive material; and wherein the sensor electrode comprises a mixture of a catalytically-active material and a conductive material.

2. The sensor of claim 1 wherein the sensor contact comprises a diffusion barrier.

3. The sensor of claim 1 wherein the solid electrolyte comprises a proton-conductive material.

4. The sensor of claim 3, wherein the proton-conductive material of the solid electrolyte comprises $[P(W_3O_{10})_4] \times H_2O$.

5. The sensor of claim 1, wherein the sensor electrode comprises a noble metal.

* * * * *

UNITED STATES PATENT AND TRADEMARK OFFICE
CERTIFICATE OF CORRECTION

PATENT NO.    : 6,074,540
DATED         : June 13, 2000
INVENTOR(S)   : Kroll et al.

Page 1 of 1

It is certified that error appears in the above-identified patent and that said Letters Patent is hereby corrected as shown below:

Column 1,
Line 36, after "easier", change "t6" to -- to --.

Column 2,
Line 15, change "german" to -- German --.
Lines 15 and 16, change "Wolframatophosphoräure-Hydrat" to
-- Wolframatophosphorsäure-Hydrat --.

Signed and Sealed this

Sixteenth Day of April, 2002

Attest:

JAMES E. ROGAN
Director of the United States Patent and Trademark Office

Attesting Officer